United States Patent
Lim et al.

(10) Patent No.: US 12,339,254 B2
(45) Date of Patent: Jun. 24, 2025

(54) ULTRASONIC TESTING APPARATUS WITH VARIABLE FREQUENCY

(71) Applicant: POSCO, Pohang-si (KR)

(72) Inventors: Choong-Soo Lim, Gwangyang-si (KR); Hyeong-Jun Huh, Gwangyang-si (KR); Sang-Jin Lee, Gwangyang-si (KR)

(73) Assignee: POSCO, Pohang-si (KR)

( * ) Notice: Subject to any disclaimer, the term of this patent is extended or adjusted under 35 U.S.C. 154(b) by 482 days.

(21) Appl. No.: 17/779,579

(22) PCT Filed: Dec. 16, 2020

(86) PCT No.: PCT/KR2020/018399
§ 371 (c)(1),
(2) Date: May 25, 2022

(87) PCT Pub. No.: WO2021/125767
PCT Pub. Date: Jun. 24, 2021

(65) Prior Publication Data
US 2023/0009623 A1 Jan. 12, 2023

(30) Foreign Application Priority Data

Dec. 18, 2019 (KR) .................... 10-2019-0169360

(51) Int. Cl.
*G01N 29/28* (2006.01)
*G01N 29/04* (2006.01)
(Continued)

(52) U.S. Cl.
CPC ............. *G01N 29/28* (2013.01); *G01N 29/04* (2013.01); *G01N 29/348* (2013.01);
(Continued)

(58) Field of Classification Search
CPC ...... G01N 29/28; G01N 29/04; G01N 29/348; G01N 33/2045; G01N 29/221;
(Continued)

(56) References Cited

U.S. PATENT DOCUMENTS 3,924,454 A 12/1975 McElroy et al.
4,558,598 A 12/1985 Young
(Continued)

FOREIGN PATENT DOCUMENTS

CN 202676673 U 1/2013
CN 105849549 A 8/2016
(Continued)

OTHER PUBLICATIONS

Extended European Search Report dated Dec. 2, 2022 issued in European Patent Application No. 20902050.2.
(Continued)

*Primary Examiner* — Jacques M Saint Surin
(74) *Attorney, Agent, or Firm* — Morgan Lewis & Bockius LLP (57) ABSTRACT

The present invention relates to an ultrasonic testing apparatus with a variable frequency, which can automatically change the frequency according to thickness and thereby detect internal defects in objects having various thicknesses. The ultrasonic testing apparatus may comprise: a nozzle jetting a medium toward an object so as to form a medium column; and a plurality of probes disposed in the nozzle so as to generate ultrasonic waves.

13 Claims, 5 Drawing Sheets

(51) Int. Cl.
*G01N 29/34* (2006.01)
*G01N 33/2045* (2019.01)

(52) U.S. Cl.
CPC . *G01N 33/2045* (2019.01); *G01N 2291/0234* (2013.01); *G01N 2291/0289* (2013.01)

(58) Field of Classification Search
CPC .. G01N 29/2431; G01N 29/043; G01N 29/27; G01N 29/24; B06B 1/20; B06B 1/0284; B06B 2291/106; B06B 2291/045; B06B 2291/2632; B06B 2291/0234; B06B 2291/0289; B06B 2201/70; G10K 11/357
USPC .......................................................... 73/628
See application file for complete search history.

(56) References Cited

U.S. PATENT DOCUMENTS

| | | | | |
|---|---|---|---|---|
| 4,599,900 | A * | 7/1986 | Friedman | G01N 29/26 73/622 |
| 5,123,433 | A * | 6/1992 | Fridsma | B08B 3/12 239/106 |
| 5,228,343 | A | 7/1993 | Schoenen et al. | |
| 5,494,038 | A * | 2/1996 | Wang | A61B 8/4281 73/644 |
| 5,628,319 | A * | 5/1997 | Koch | G01N 29/11 600/437 |
| 7,431,697 | B2 * | 10/2008 | Irioka | H03M 1/308 600/445 |
| 8,783,111 | B2 * | 7/2014 | Matsumoto | G01N 29/11 73/632 |
| 10,209,228 | B2 * | 2/2019 | Oono | G01N 29/225 |
| 10,502,712 | B2 * | 12/2019 | Hall | G01N 29/28 |
| 2008/0041159 | A1 | 2/2008 | Koester et al. | |
| 2009/0126496 | A1 | 5/2009 | Maurer et al. | |
| 2012/0192651 | A1 | 8/2012 | Lee et al. | |
| 2016/0109416 | A1 | 4/2016 | Sohn et al. | |
| 2016/0320345 | A1 | 11/2016 | Lim et al. | |
| 2018/0168549 | A1 | 6/2018 | Burchardt | |
| 2018/0172644 | A1 | 6/2018 | Sylvestre et al. | |
| 2018/0340914 | A1 | 11/2018 | Lim et al. | |

FOREIGN PATENT DOCUMENTS

| | | |
|---|---|---|
| CN | 108291895 A | 7/2018 |
| JP | H5-024052 Y2 | 6/1993 |
| JP | 2004-271351 A | 9/2004 |
| JP | 2006-292697 A | 10/2006 |
| JP | 2018-536164 A | 12/2018 |
| KR | 10-1414520 B1 | 7/2014 |
| KR | 10-2015-0075496 A | 7/2015 |
| KR | 10-1618158 B1 | 5/2016 |
| KR | 10-1736612 B1 | 5/2017 |

OTHER PUBLICATIONS

International Search Report dated Mar. 5, 2021 issued in International Patent Application No. PCT/KR2020/018399 (with English translation).

Japanese Office Action dated May 9, 2023 issued in Japanese Patent Application No. 2022-536834.

Office Action dated Jan. 14, 2025, issued in corresponding Chinese Patent Application No. 202080087439.6 with an English translation.

\* cited by examiner

ULTRASONIC TESTING APPARATUS WITH VARIABLE FREQUENCY

CROSS-REFERENCE OF RELATED APPLICATIONS

This application is the U.S. National Phase under 35 U.S.C. § 371 of International Patent Application No. PCT/KR2020/018399, filed on Dec. 16, 2020, which in turn claims the benefit of Korean Application No. 10-2019-0169360, filed on Dec. 18, 2019, the entire disclosures of which applications are incorporated by reference herein.

TECHNICAL FIELD

The present disclosure relates to an ultrasonic testing apparatus with a variable frequency capable of detecting internal defects in objects having various thicknesses by automatically changing the frequency according to thickness.

BACKGROUND ART

For example, in a thick plate line of a steel mill, ultrasonic testing has been performed in a correction line before shipment to ensure quality of products that have been produced. The ultrasonic testing diagnoses whether defects, such as cracks, inclusions and segregations are present in products by transmitting ultrasonic waves to the products and receiving and analyzing the ultrasonic waves reflected from the products.

During the ultrasonic testing, gaps between surfaces of products and probes are filled with water and then ultrasonic waves are transmitted. Contact media are required to transmit ultrasonic energy oscillated from the probes to the products. Among the contact media, water is a representative medium with excellent ultrasonic transmission efficiency.

Meanwhile, thick plates having various thicknesses are being produced as products in a thick plate factory of a steel mill. Ultrasonic waves are scattered or absorbed while propagating inside metal, so their energy is reduced. The degree of reduction in energy varies according to frequencies of ultrasonic waves and a type and grain structure of metal.

In consideration of such ultrasonic attenuation, a standard of ultrasonic testing is established. For example, for products with a thickness of 80 mm or less, ultrasonic waves having a frequency of about 5 MHz are applied, and for products with a thickness more than 80 mm, ultrasonic waves having about 2 MHz are applied.

Accordingly, there is a problem in that a 5 MHz ultrasonic tester and a 2 MHz ultrasonic tester are separately provided for testing all products of various thicknesses, and need to be selectively used according to thickness. Usually, since an ultrasonic tester for testing a full width of a product is very expensive as the ultrasonic tester includes hundreds of ultrasonic sensors, signal processing arrays, and defect determination software, installing two testers requires a lot of money and manpower, and maintenance costs increase as the number of devices increases.

As related art, there is an invention disclosed in Japanese Unexamined Utility Model Publication No. 63-200161 U.

DISCLOSURE

Technical Problem

An aspect of the present disclosure is to provide an ultrasonic testing apparatus with a variable frequency capable of detecting internal defects in objects having various thicknesses by automatically changing the frequency according to thickness.

Technical Solution

According to an aspect of the present disclosure, an ultrasonic testing apparatus includes: a nozzle jetting a medium towards an object to form a medium column; and a plurality of probes disposed on the nozzle to oscillate an ultrasonic wave.

The ultrasonic testing apparatus may further include an ultrasonic reflector rotatably installed in the nozzle so that an ultrasonic wave of a probe selected from the plurality of probes is transmitted to the object.

The ultrasonic testing apparatus may further include a plurality of inlet waveguides branched from the outlet waveguide and having the plurality of probes distributed to each of the plurality of inlet waveguides, in which the nozzle is formed of one outlet waveguide.

Advantageous Effects

As set forth above, according to an exemplary embodiment in the present disclosure, one ultrasonic testing apparatus may detect internal defects in all products having various thicknesses, so it is possible to greatly save installation and operation costs and manpower of the ultrasonic testing apparatus.

In addition, according to an exemplary embodiment in the present disclosure, one ultrasonic testing apparatus may test all products, so it is possible to more efficiently integrate and manage internal defects in products compared to the case where a plurality of ultrasonic testers are operated, to thereby improve quality and productivity of the products.

BEST MODE

Hereinafter, the present disclosure will be described in detail with reference to the exemplary drawings. It is to be noted that in giving reference numerals to components of the accompanying drawings, the same components will be denoted by the same reference numerals even though they are illustrated in different drawings. Further, in describing exemplary embodiments in the present disclosure, well-known functions or constructions will not be described in detail since they may unnecessarily obscure the understanding of the present disclosure.

Figure 1:
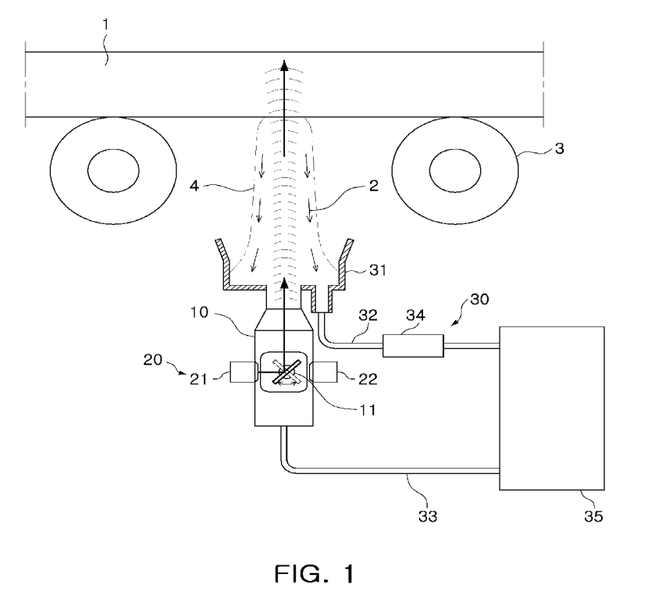
FIG. 1 is a diagram schematically illustrating an ultrasonic testing apparatus according to a first exemplary embodiment in the present disclosure.
Figure 2:
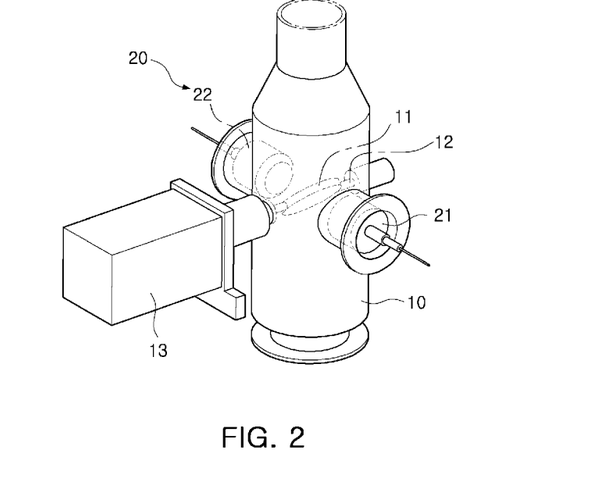
FIG. 2 is a perspective view illustrating a main part of the ultrasonic testing apparatus according to the first exemplary embodiment in the present disclosure.
Figure 3:
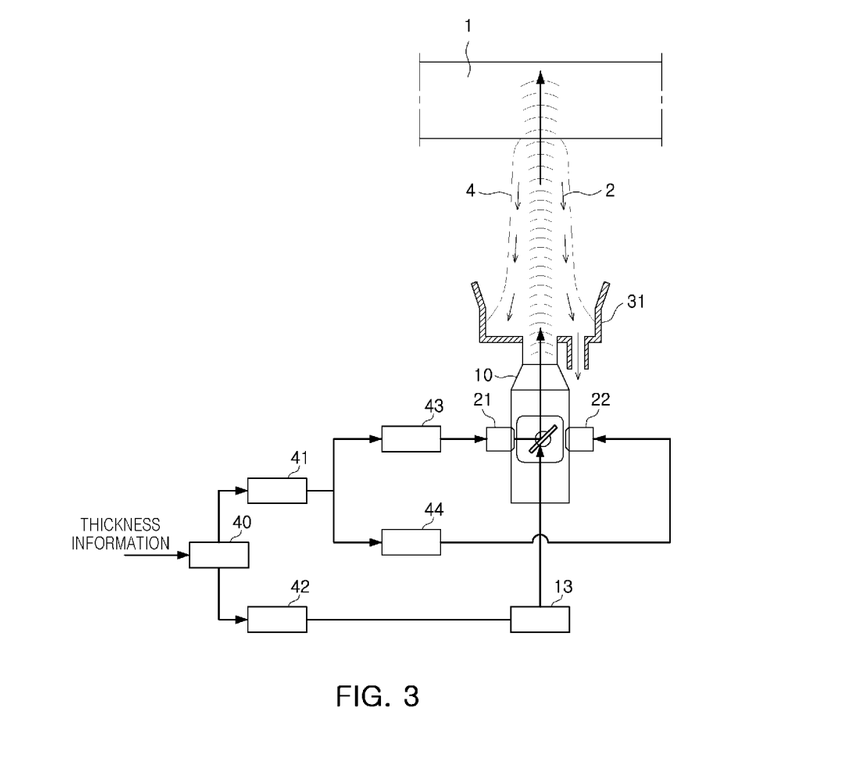
FIG. 3 is a diagram for describing a control process of the ultrasonic testing apparatus according to the first exemplary embodiment in the present disclosure.

FIG. 1 is a diagram schematically illustrating an ultrasonic testing apparatus according to a first exemplary embodiment in the present disclosure, FIG. 2 is a perspective view illustrating a main part of the ultrasonic testing apparatus according to the first exemplary embodiment in the present disclosure, and FIG. 3 is a diagram for describing a control process of the ultrasonic testing apparatus according to the first exemplary embodiment in the present disclosure.

As illustrated in these drawings, the ultrasonic testing apparatus according to the first exemplary embodiment in the present disclosure may include a nozzle 10 and a plurality of probes 20, 21, and 22.

The nozzle 10 may be installed on a lower side of an object 1 such as a thick steel plate conveyed by a conveyance means, for example, a guide roll 3, and jet a medium 2 (for example, water) toward the object to form a medium column 4 (for example, a water column).

Such a nozzle 10 should be able to form a stable medium column 4 in close contact with a lower surface of the object 1. To this end, an inner diameter of the nozzle is limited.

When the inner diameter of the nozzle 10 increases, a volume and mass of the medium column 4 increase, so a height of the medium column suddenly decreases. In addition, since a pulsation is formed inside the medium column, it becomes difficult to stably transmit ultrasonic waves.

On the other hand, when the inner diameter of the nozzle 10 is too small, as a testing area becomes small and a flow rate increases, a flow of the medium 2 becomes unstable, so it is not possible to stably transmit ultrasonic waves.

Accordingly, the relationship between an inner diameter d of the nozzle 10 and a width w or diameter of a probe surface needs to satisfy the following [Equation 1]. In this case, the most stable ultrasonic testing is possible. Here, the probe surface refers to a surface on which the ultrasonic waves are substantially oscillated by the probe 20.

$$d/2 < w < d \qquad \text{[Equation 1]}$$

In the ultrasonic testing apparatus according to the first exemplary embodiment in the present disclosure, frequency switching is possible using one nozzle 10 having the inner diameter d of a correlation as in the above Equation 1 with respect to the width w or diameter of the probe surface.

The medium column 4 may be formed to have a height of several tens of millimeters (mm) from an outlet of the nozzle 10, and the transmission and reception of ultrasonic waves is possible through this medium column. Since water is employed as a medium having excellent ultrasonic transmission efficiency, the medium column may be formed of a water column.

The ultrasonic testing apparatus according to the first exemplary embodiment in the present disclosure may further include a medium circulation unit 30 that forms the medium column 4 by jetting the medium 2 from the nozzle 10, recovering the medium falling from the medium column, and circulating the medium back to the nozzle.

The medium circulation unit 30 may include a medium receiver 31, a recovery pipe 32, and a supply pipe 33.

The medium receiver 31 may be installed outside the nozzle 10 and may be configured to receive the medium 2 that has fallen from the medium column 4. The medium receiver may be formed in a cylindrical shape or a box shape surrounding the nozzle.

The recovery pipe 32 may be connected to the medium receiver 31 and may be configured to recover the medium 2 in the medium receiver. The medium falling from the medium column 4 and collected in the medium receiver may be supplied to the recovery pipe.

A filter 34 for filtering the medium 2 discharged from the medium receiver 32 may be installed in the recovery pipe 32, so the medium from which impurities have been removed may be re-supplied to the nozzle 10.

The supply pipe 33 is for supplying the medium of the recovery pipe 32 to the nozzle 10, and may communicate with the nozzle 10 and the recovery pipe 32, respectively.

A circulation pump 35 providing jetting pressure to the nozzle 10 may be installed between the recovery pipe 32 and the supply pipe 33. The medium column 4 may be formed by allowing the nozzle to jet the medium 2 at a constant pressure according to the pressure provided by the circulation pump. By controlling the circulation pump, the jetting pressure of the nozzle may be controlled.

The plurality of probes 20 may be disposed on the nozzle 10 to oscillate ultrasonic waves.

Specifically, each of the plurality of probes 20 may be fixedly installed to be spaced apart from each other on a sidewall of the nozzle 10, and may transmit and receive ultrasonic waves for detecting internal defects in the object 1 through the medium column 4. FIGS. 1 to 3 illustrate an example in which two probes 21 and 22 are mounted symmetrically with respect to the nozzle.

The plurality of probes 20 may oscillate ultrasonic waves having different frequencies. For example, one probe 21 may oscillate an ultrasonic wave having a frequency of about 5 MHz, and the other probe 22 may oscillate an ultrasonic wave having a frequency of about 2 MHz.

Each of these probes 20 may be connected to, through wired and wireless communication, a defect detection unit (not illustrated) that processes and calculates an ultrasonic signal received from the object 1 to analyze whether internal defects are present in an object.

In addition, the ultrasonic testing apparatus according to the first exemplary embodiment in the present disclosure may include an ultrasonic reflector 11 that is rotatably installed between the plurality of probes in the nozzle so that an ultrasonic wave of a probe selected from the plurality of probes 20 is transmitted to the object 1.

The ultrasonic reflector 11 may be made of, for example, a metal material such as stainless steel and brass, and thus, may smoothly reflect ultrasonic waves, and may not be corroded by the medium 2 such as water.

The ultrasonic reflector 11 may be fixed to a rotation shaft 12 installed across the inside of the nozzle 10, and the rotation shaft may be exposed to the outside through a sidewall of the nozzle 10. A motor 13 installed outside the nozzle may be connected to one end of the rotation shaft, so a rotation angle of the ultrasonic reflector may be controlled.

As such, the rotation angle may be controlled by the motor 13, so the ultrasonic reflector 11 may selectively transmit ultrasonic waves oscillated from both probes 20 toward the object 1.

A control process for automatically switching a frequency of an ultrasonic wave in the ultrasonic testing apparatus according to the first exemplary embodiment in the present disclosure will be described with reference to FIG. 3.

For example, in a correction line of the thick plate factory of the steel mill, a product which is the object 1 subjected to the ultrasonic testing is conveyed to the ultrasonic testing apparatus by the guide roll 3. Before an object enters the ultrasonic testing apparatus, a main controller 40 constituting a factory operation system may receive thickness information of the object.

The main controller 40 may transmit the received thickness information to an on-off controller 41 for probe.

The on-off controller 41 for probe may select one of the plurality of probes 20 based on the thickness information of the object 1 to be subjected to the ultrasonic testing according to its internal program.

When the thickness of the object 1 is, for example, 80 mm or less, a command is transmitted to a first pulser receiver 43 corresponding to one probe 21 that oscillates an ultrasonic wave having a frequency of about 5 MHz to operate the first pulser receiver 43 and stop an operation of a second pulser receiver 44 of the other probe 22.

On the other hand, when the thickness of the object 1 exceeds, for example, 80 mm, a command is transmitted to the second pulser receiver 44 corresponding to the other probe 22 that oscillates an ultrasonic wave having a frequency of about 2 MHz to operate the second pulser receiver 44 and stop the operation of the first pulser receiver 43.

In addition, the main controller 40 may transmit the received thickness information to a direction controller 42 for an ultrasonic reflector.

The direction controller 42 for the ultrasonic reflector may control a rotation angle of the ultrasonic reflector by operating the motor 13 according to the transmitted thickness information and switch an inclination direction of the ultrasonic reflector.

In other words, when the thickness of the object 1 is, for example, 80 mm or less, the inclination direction of the ultrasonic reflector 11 so that an ultrasonic wave having a frequency of about 5 MHz oscillated from one probe 21 is reflected toward the outlet of the nozzle 10 and a lower surface of the object is changed.

On the other hand, when the thickness of the object 1 exceeds, for example, 80 mm, the inclination direction of the ultrasonic reflector 11 so that an ultrasonic wave having a frequency of about 2 MHz oscillated from the other probe 22 is reflected toward the outlet of the nozzle 10 and the lower surface of the object is changed.

In the ultrasonic testing apparatus according to the first exemplary embodiment in the present disclosure, the plurality of probes 20 oscillating ultrasonic waves having different frequencies are symmetrically mounted on the nozzle 10, and by controlling the rotation angle of the ultrasonic reflector 11 located between the probes so that the ultrasonic wave of the selected frequency according to the thickness of the object 1 is transmitted to an object, the frequency of the ultrasonic wave may be automatically switched according to the thickness of the object.

Therefore, in the ultrasonic testing apparatus according to the first exemplary embodiment in the present disclosure, it is possible to easily switch the frequency of the ultrasonic wave and to stably transmit/receive the ultrasonic wave.

Figure 4:
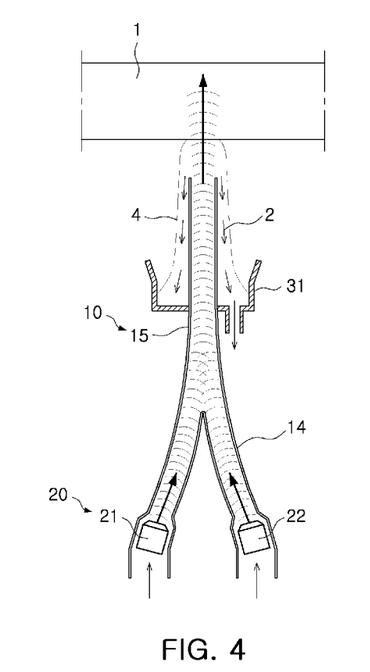
FIG. 4 is a cross-sectional view illustrating a main part of an ultrasonic testing apparatus according to a second exemplary embodiment in the present disclosure.
Figure 5:
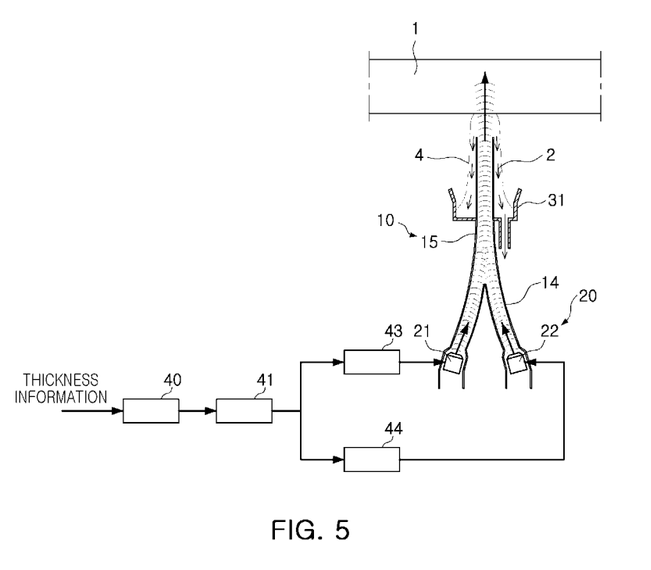
FIG. 5 is a diagram for describing a control process of the ultrasonic testing apparatus according to the second exemplary embodiment in the present disclosure.

FIG. 4 is a cross-sectional view illustrating a main part of an ultrasonic testing apparatus according to a second exemplary embodiment in the present disclosure and FIG. 5 is a diagram for describing a control process of the ultrasonic testing apparatus according to the second exemplary embodiment in the present disclosure.

The second exemplary embodiment in the present disclosure illustrated in FIGS. 4 and 5 is different from the first embodiment illustrated in FIGS. 1 to 3 described above in terms of only the shape of the nozzle without the ultrasonic reflector and the motor and the arrangement relationship of the probes, and the remaining components are the same as those of the first embodiment. Therefore, in describing the ultrasonic testing apparatus according to the second exemplary embodiment in the present disclosure, the same components as those of the ultrasonic testing apparatus according to the first embodiment will be denoted by the same reference numerals, and a detailed description for configurations and functions of these components will be omitted.

In the ultrasonic testing apparatus according to the second exemplary embodiment in the present disclosure, the nozzle 10 may be formed of one outlet waveguide 15 and branched from the outlet waveguide, and the plurality of probes 20 may further include a plurality of inlet waveguides 14 distributed to each of the plurality of probes 20.

Each of the plurality of probes 20 may be installed inside the corresponding inlet waveguide 14, and may transmit and receive ultrasonic waves for detecting internal defects in the object 1 through the medium column 4.

As in the first embodiment described above, these probes 20 may oscillate ultrasonic waves having different frequencies. For example, one probe 21 may oscillate an ultrasonic wave having a frequency of about 5 MHz, and the other probe 22 may oscillate an ultrasonic wave having a frequency of about 2 MHz.

Each of these probes 20 may be connected to, through wired and wireless communication, the defect detection unit (not illustrated) that processes and calculates the ultrasonic signal received from the object 1 to analyze whether the internal defects exist in the object.

The ultrasonic waves oscillated from the probes 20 in each inlet waveguide 14 may be propagated out of the nozzle 10 through the outlet waveguide 15.

The medium 2 may also be supplied to the inlet waveguide 14 through a branched supply pipe (not illustrated), and then may be jetted out of the nozzle 10 via the outlet waveguide 15 through a common path.

Preferably, the total reflection condition between the ultrasonic wave and the inner interface of the waveguide needs to be satisfied so that the ultrasonic wave introduced into the inlet waveguide 14 is propagated without loss in the outlet waveguide 15. That is, the loss of ultrasonic energy in the waveguide needs to be minimized.

To this end, as in the following Equation 2, an ultrasonic velocity $V_1$ in the medium in the waveguide needs to be smaller than an ultrasonic velocity $V_2$ in the inner interface of the waveguide.

$$V_1 < V_2 \qquad \text{[Equation 2]}$$

Equation 2 may be satisfied when the medium 2 such as water is filled inside the waveguide, and the inlet waveguide 14 and the outlet waveguide 15 are made of a metal material.

In addition, since a curved or bent surface is formed at a portion in which the plurality of inlet waveguides 14 are coupled to one outlet waveguide 15, an angle between the ultrasonic wave and the inner interface of the waveguide is changed.

In the portion in which the angle is changed as described above, that is, in the portion in which the plurality of inlet waveguides 14 are coupled to one outlet waveguide 15, when the inlet waveguide and the outlet waveguide are designed so that an angle (incident angle: θ) between a propagation direction of the ultrasonic wave traveling from the inlet waveguide to the outlet waveguide and a direction perpendicular to the inner interface of the outlet waveguide is greater than a critical angle θc, the ultrasonic waves may be transmitted through the outlet waveguide without loss.

In other words, as in the following Equation 3, when the ultrasonic waves are incident on the inner interface of the waveguide at the angle θ greater than the critical angle θc, the total reflection occurs.

$$\theta c < \theta \qquad \text{[Equation 3]}$$

Here, the critical angle may be expressed as in the following Equation 4.

$$\theta_C = \arcsin\left(\frac{V_1}{V_2}\right) \qquad \text{[Equation 4]}$$

Therefore, in the ultrasonic testing apparatus according to the second exemplary embodiment in the present disclosure, one outlet waveguide 15 and the plurality of inlet waveguides 14 constituting the nozzle 10 may be designed under the condition satisfying the above Equations 2 and 3, and when the plurality of probes 20 selectively oscillate ultrasonic waves having different frequencies, the ultrasonic testing of the object 1 having various thicknesses becomes possible.

A control process for automatically switching a frequency of an ultrasonic wave in the ultrasonic testing apparatus according to the second exemplary embodiment in the present disclosure will be described with reference to FIG. 5.

For example, in the correction line of the thick plate factory of the steel mill, the product which is the object 1 subjected to the ultrasonic testing is conveyed to the ultrasonic testing apparatus by the guide roll 3. Before the object enters the ultrasonic testing apparatus, the main controller 40 constituting the factory operation system may receive the thickness information of the object.

The main controller 40 may transmit the received thickness information to the on-off controller 41 for probe.

The on-off controller 41 for probe may select one of the plurality of probes 20 based on the thickness information of the object 1 to be subjected to the ultrasonic testing according to its internal program.

When the thickness of the object 1 is, for example, 80 mm or less, a command is transmitted to the first pulser receiver 43 corresponding to one probe 21 that oscillates an ultrasonic wave having a frequency of about 5 MHz to operate the first pulser receiver 43 and stop the operation of the second pulser receiver 44 of the other probe 22.

On the other hand, when the thickness of the object 1 exceeds, for example, 80 mm, a command is transmitted to the second pulser receiver 44 corresponding to the other probe 22 that oscillates an ultrasonic wave having a frequency of about 2 MHz to operate the second pulser receiver 44 and stop the operation of the first pulser receiver 43.

In the ultrasonic testing apparatus according to the second exemplary embodiment in the present disclosure, each of the probes 20 oscillating ultrasonic waves having different frequencies may be mounted on the plurality of inlet waveguides 14 of the nozzle 10, and the operation of the probe 20 may be selectively controlled so that the ultrasonic wave of the frequency selected according to the thickness of the object 1 is transmitted to the object through the outlet waveguide 15, so the frequency of the ultrasonic wave may be automatically switched according to the thickness of the object.

Therefore, in the ultrasonic testing apparatus according to the second exemplary embodiment in the present disclosure, it is possible to easily switch the frequency of the ultrasonic wave and to stably transmit/receive the ultrasonic wave.

As described above, according to the present disclosure, the frequency of the ultrasonic wave may be automatically selected according to the thickness of the object and then the ultrasonic wave may be transmitted to the lower surface of the object through the nozzle, so the internal defects in objects having various thicknesses through one ultrasonic testing apparatus may be detected.

The spirit of the present disclosure has been illustratively described hereinabove. It will be appreciated by those skilled in the art that various modifications and alterations may be made without departing from the essential characteristics of the present disclosure. Accordingly, embodiments disclosed in the present disclosure and the drawings are not to limit the spirit of the present disclosure, but are to describe the spirit of the present disclosure. The scope of the present disclosure is not limited to these embodiments. The scope of the present disclosure should be interpreted by the following claims, and it should be interpreted that all the spirits equivalent to the following claims fall within the scope of the present disclosure.

INDUSTRIAL APPLICABILITY

As described above, the present disclosure is useful for ultrasonic testing performed on products that have been produced in a thick plate factory of a steel mill, for example.

The invention claimed is:

1. An ultrasonic testing apparatus, comprising:
   a nozzle jetting a medium towards an object to form a medium column; and
   a plurality of probes disposed on the nozzle to oscillate an ultrasonic wave, and
   an ultrasonic reflector rotatably installed between the plurality of probes in the nozzle so that an ultrasonic wave of a probe selected from the plurality of probes is transmitted to the object.

2. The ultrasonic testing apparatus of claim 1, wherein a relationship between an inner diameter d of the nozzle and a width w or a diameter of a probe surface of a probe is established in the following [Equation 1]

$$d/2 < w < d \qquad \text{[Equation 1]}.$$

3. The ultrasonic testing apparatus of claim 1, wherein the plurality of probes oscillate ultrasonic waves having different frequencies.

4. The ultrasonic testing apparatus of claim 3, wherein the plurality of probes are fixedly installed to be spaced apart from each other on a sidewall of the nozzle.

5. The ultrasonic testing apparatus of claim 1, wherein the ultrasonic reflector comprises a material reflecting ultrasonic waves and which is not corroded by the medium.

6. The ultrasonic testing apparatus of claim 1, wherein the ultrasonic reflector is fixed to a rotation shaft installed across an inside of the nozzle, and a motor installed outside the nozzle is connected to one end of the rotation shaft.

7. The ultrasonic testing apparatus of claim 6, further comprising:
   a main controller receiving thickness information of the object;
   an on-off controller for a probe selecting the probe from the plurality of probes based on the thickness information of the object transmitted from the main controller;
   a first pulser receiver and a second pulser receiver selectively oscillating an ultrasonic wave of a corresponding probe according to a command of the on-off controller for probe; and
   a direction controller for an ultrasonic reflector controlling a rotation angle of the ultrasonic reflector by operating the motor based on the thickness information of the object transmitted from the main controller.

8. The ultrasonic testing apparatus of claim 1, further comprising:

a medium circulation unit forming a medium column by jetting the medium from the nozzle, recovering the medium falling from the medium column, and circulating the medium back to the nozzle.

9. The ultrasonic testing apparatus of claim 8, wherein the medium circulation unit includes:
a medium receiver installed outside the nozzle and receiving the medium falling from the medium column;
a recovery pipe connected to the medium receiver;
a supply pipe supplying the medium of the recovery pipe to the nozzle; and
a circulation pump installed between the recovery pipe and the supply pipe to provide jetting pressure to the nozzle.

10. An ultrasonic testing apparatus, comprising:
a nozzle jetting a medium towards an object to form a medium column;
a plurality of probes disposed on the nozzle to oscillate an ultrasonic wave; and
a plurality of inlet waveguides,
wherein the nozzle includes one outlet waveguide,
the plurality of inlet waveguides are branched from the outlet waveguide and having the plurality of probes distributed to each of the plurality of inlet waveguides.

11. The ultrasonic testing apparatus of claim 10, wherein the plurality of probes are respectively installed inside the corresponding inlet waveguide, and
the medium supplied to the inlet waveguide is jetted through the outlet waveguide.

12. The ultrasonic testing apparatus of claim 10, wherein an ultrasonic velocity $V_1$ in a medium in the waveguide is smaller than an ultrasonic velocity $V_2$ in an inner interface of the waveguide, and
in a portion in which the plurality of inlet waveguides are coupled to one outlet waveguide, an angle θ between a propagation direction of the ultrasonic wave traveling from the inlet waveguide to the outlet waveguide and a direction perpendicular to an inner interface of the outlet waveguide is greater than a critical angle θc, and the critical angle θc is defined by the following Equation 2, $$\theta_C = \arcsin\left(\frac{V_1}{V_2}\right).$$ [Equation 2]

13. The ultrasonic testing apparatus of claim 10, further comprising:
a main controller receiving thickness information of the object;
an on-off controller for probe selecting the probe from the plurality of probes based on the thickness information of the object transmitted from the main controller; and
a first pulser receiver and a second pulser receiver selectively oscillating an ultrasonic wave of a corresponding probe according to a command of the on-off controller for probe.

* * * * *